United States Patent
Krause et al.

(10) Patent No.: US 10,040,009 B1
(45) Date of Patent: *Aug. 7, 2018

(54) FILTER CARTRIDGE

(71) Applicant: Haier US Appliance Solutions, Inc., Wilmington, DE (US)

(72) Inventors: Andrew Reinhard Krause, Louisville, KY (US); Gregory Sergeevich Chernov, Louisville, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,932

(22) Filed: Jun. 27, 2017

(51) Int. Cl.
| | | |
|---|---|---|
| *B01D 35/14* | (2006.01) | |
| *B01D 35/143* | (2006.01) | |
| *C02F 1/00* | (2006.01) | |
| *B01D 35/30* | (2006.01) | |
| *A61F 13/42* | (2006.01) | |

(52) U.S. Cl.
CPC ............ *B01D 35/143* (2013.01); *A61F 13/42* (2013.01); *B01D 35/30* (2013.01); *C02F 1/001* (2013.01); *C02F 1/003* (2013.01); *B01D 2201/56* (2013.01)

(58) Field of Classification Search
CPC .. B01D 35/143; B01D 35/1435; B01D 35/30; B01D 2201/56; F01M 11/03; F01M 11/04; F02M 37/221; C02F 1/001; C02F 1/003; G06K 7/10366; A61F 13/42
USPC .................. 340/10.5, 10.42, 572.9
See application file for complete search history.

(56) References Cited

U.S. PATENT DOCUMENTS

| | | |
|---|---|---|
| 3,995,636 A | 12/1976 | Murray et al. |
| 4,855,077 A | 8/1989 | Shikinami et al. |
| 5,089,144 A | 2/1992 | Ozkahyaoglu et al. |
| 5,171,430 A | 12/1992 | Beach et al. |
| 5,190,666 A | 3/1993 | Bisconte |
| 5,192,424 A | 3/1993 | Beyne et al. |
| 5,328,597 A | 7/1994 | Boldt, Jr. et al. |
| 5,536,264 A | 7/1996 | Hsueh et al. |
| 5,907,958 A | 6/1999 | Coates et al. |
| 6,009,404 A | 12/1999 | Eimer |
| 6,051,144 A | 4/2000 | Clack et al. |
| 6,139,738 A | 10/2000 | Maxwell |
| 6,303,031 B1 | 10/2001 | Senner |

(Continued)

FOREIGN PATENT DOCUMENTS

| | | |
|---|---|---|
| EP | 1936305 A2 | 6/2008 |
| JP | 2001016025 A | 1/2001 |

(Continued)

OTHER PUBLICATIONS

PCT Search Report and Written Opinion PCT/US2014/056282, dated Nov. 27, 2014. (11 pages).

(Continued)

*Primary Examiner* — Ali Neyzari
(74) *Attorney, Agent, or Firm* — Dority & Manning, P.A.

(57) ABSTRACT

A filter cartridge includes a radio frequency identification tag positioned at an outer surface of a casing. The radio frequency identification tag includes an antenna and an integrated circuit. The antenna, the integrated circuit or both the antenna and the integrated circuit are fixedly connected to one or more of the casing, a water absorbent material and a fiber fabric positioned over the radio frequency identification tag on the outer surface of the casing.

20 Claims, 10 Drawing Sheets

(56) References Cited

U.S. PATENT DOCUMENTS

| | | |
|---|---|---|
| 6,355,177 B2 | 3/2002 | Senner et al. |
| 6,533,926 B2 | 3/2003 | Hawkins et al. |
| 6,537,444 B2 | 3/2003 | Wilberscheid et al. |
| 6,551,503 B2 | 4/2003 | Niers et al. |
| 6,753,783 B2 | 6/2004 | Friedman et al. |
| 6,865,941 B2 | 3/2005 | Gibbs |
| 6,950,032 B1 | 9/2005 | Hewitt et al. |
| 7,067,054 B2 | 6/2006 | Fritze |
| RE39,361 E | 10/2006 | Den Dekker |
| 7,481,917 B2 | 1/2009 | Ikeyama et al. |
| 7,638,042 B2 | 12/2009 | Astle et al. |
| 7,736,495 B2 | 6/2010 | Ikeyama et al. |
| 7,836,708 B2 | 11/2010 | Krause et al. |
| 7,855,649 B2 | 12/2010 | Masin |
| 8,118,997 B2 | 2/2012 | Ebrom et al. |
| 8,169,318 B2 | 5/2012 | Atherton |
| 8,196,809 B2 | 6/2012 | Thorstensson |
| 8,216,463 B1 | 7/2012 | Baird |
| 8,242,893 B1 | 8/2012 | Lin |
| 8,282,820 B2 | 10/2012 | Cur et al. |
| 8,289,173 B2 | 10/2012 | Ben-Mansour et al. |
| 8,427,316 B2 | 4/2013 | Bielas |
| 8,695,371 B2 | 4/2014 | Boarman et al. |
| 8,746,003 B2 | 6/2014 | Yoon |
| 8,893,976 B1 | 11/2014 | Lindblad et al. |
| 8,991,709 B2 | 3/2015 | Mieslinger |
| 9,361,776 B2 | 6/2016 | Teeter |
| 2002/0189983 A1 | 12/2002 | Guess et al. |
| 2004/0001991 A1 | 1/2004 | Kinkelaar et al. |
| 2004/0007516 A1 | 1/2004 | Fritze et al. |
| 2004/0251210 A1 | 12/2004 | Fritze et al. |
| 2005/0092070 A1 | 5/2005 | Bhatti |
| 2005/0167352 A1 | 8/2005 | Burrows et al. |
| 2005/0194317 A1 | 9/2005 | Ikeyama et al. |
| 2006/0011523 A1 | 1/2006 | Schrott et al. |
| 2006/0060512 A1 | 3/2006 | Astle et al. |
| 2006/0186031 A1 | 8/2006 | Fick et al. |
| 2008/0094220 A1 | 4/2008 | Foley et al. |
| 2010/0100026 A1 | 4/2010 | Morris |
| 2010/0275633 A1 | 11/2010 | An et al. |
| 2011/0036109 A1 | 2/2011 | Krause et al. |
| 2011/0062060 A1 | 3/2011 | Royal et al. |
| 2011/0306782 A1 | 12/2011 | Taillefer et al. |
| 2012/0297817 A1 | 11/2012 | Krause et al. |
| 2013/0008838 A1 | 1/2013 | Burke et al. |
| 2013/0068673 A1 | 3/2013 | Maggiore et al. |
| 2013/0075479 A1 | 3/2013 | Mieslinger |
| 2013/0143004 A1 | 6/2013 | Takashima et al. |
| 2013/0299588 A1 | 7/2013 | Lin |
| 2013/0240431 A1 | 9/2013 | Foix et al. |
| 2014/0110331 A1 | 4/2014 | Baird |
| 2014/0200538 A1* | 7/2014 | Euliano .................. A61F 13/42 604/361 |
| 2014/0305930 A1 | 10/2014 | Heizer et al. |
| 2014/0353235 A1 | 12/2014 | Sherman et al. |
| 2015/0102931 A1 | 4/2015 | Chernov et al. |
| 2015/0290567 A1 | 10/2015 | Chernov et al. |
| 2015/0290568 A1 | 10/2015 | Chernov et al. |
| 2015/0290569 A1 | 10/2015 | Chernov et al. |

FOREIGN PATENT DOCUMENTS

| | | |
|---|---|---|
| JP | 2003192096 A | 7/2003 |
| JP | 2006258684 A | 9/2006 |
| JP | 2007147356 A | 6/2007 |
| JP | 2007163255 A | 6/2007 |
| KR | 20120120844 A | 11/2012 |
| WO | WO83/02523 A1 | 7/1983 |
| WO | WO97/38272 A1 | 10/1997 |
| WO | WO03/011426 A1 | 2/2003 |
| WO | WO03/084875 A1 | 10/2003 |
| WO | WO2004/037383 A1 | 5/2004 |
| WO | WO2006/093657 A2 | 9/2006 |
| WO | WO2008/125530 A1 | 10/2008 |
| WO | WO2013/13004 A1 | 10/2013 |

OTHER PUBLICATIONS

PCT Search Report and Written Opinion PCT/US2014/060223, dated Jan. 23, 2015. (9 pages).

* cited by examiner

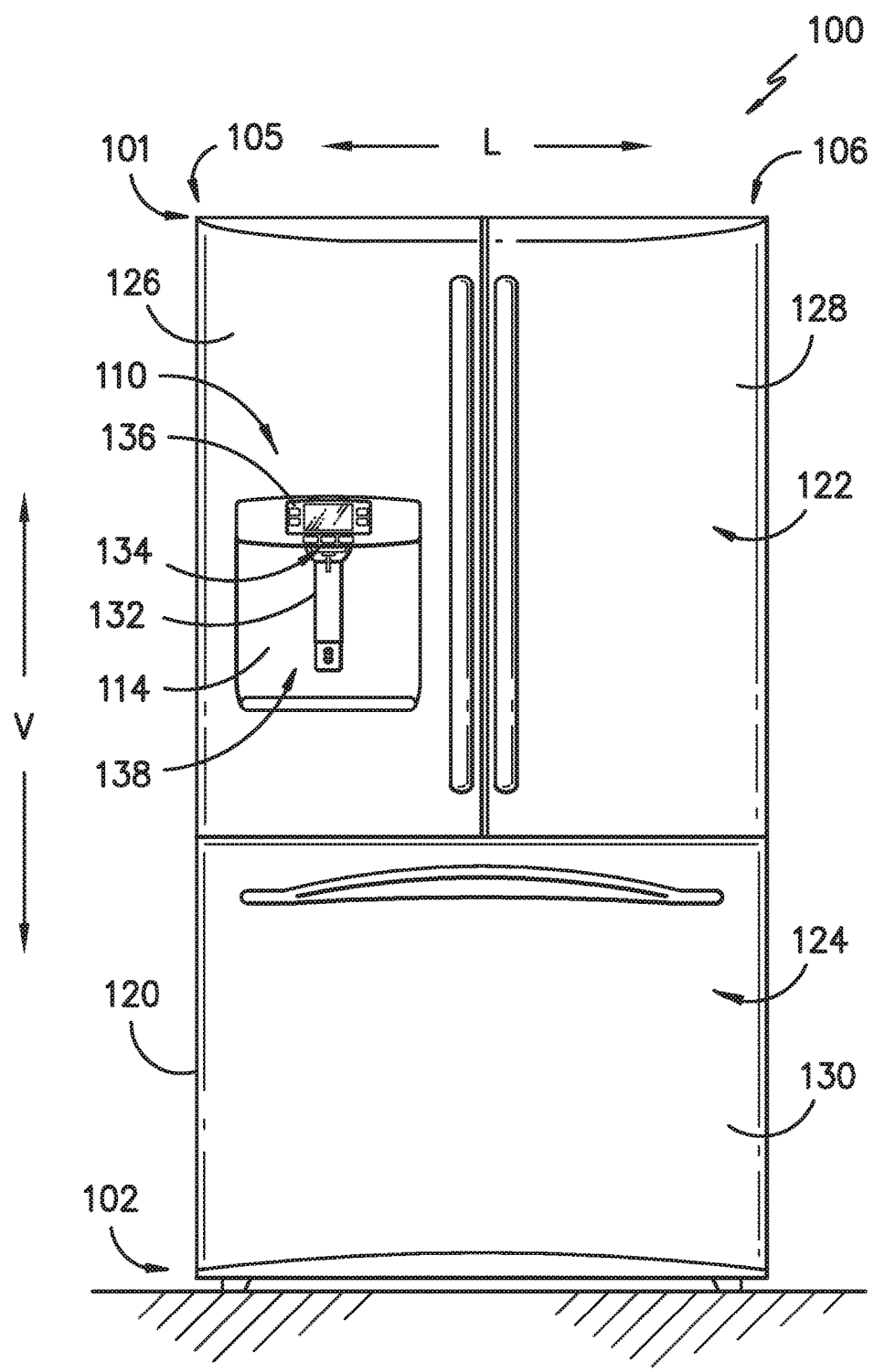
FIG. -1-

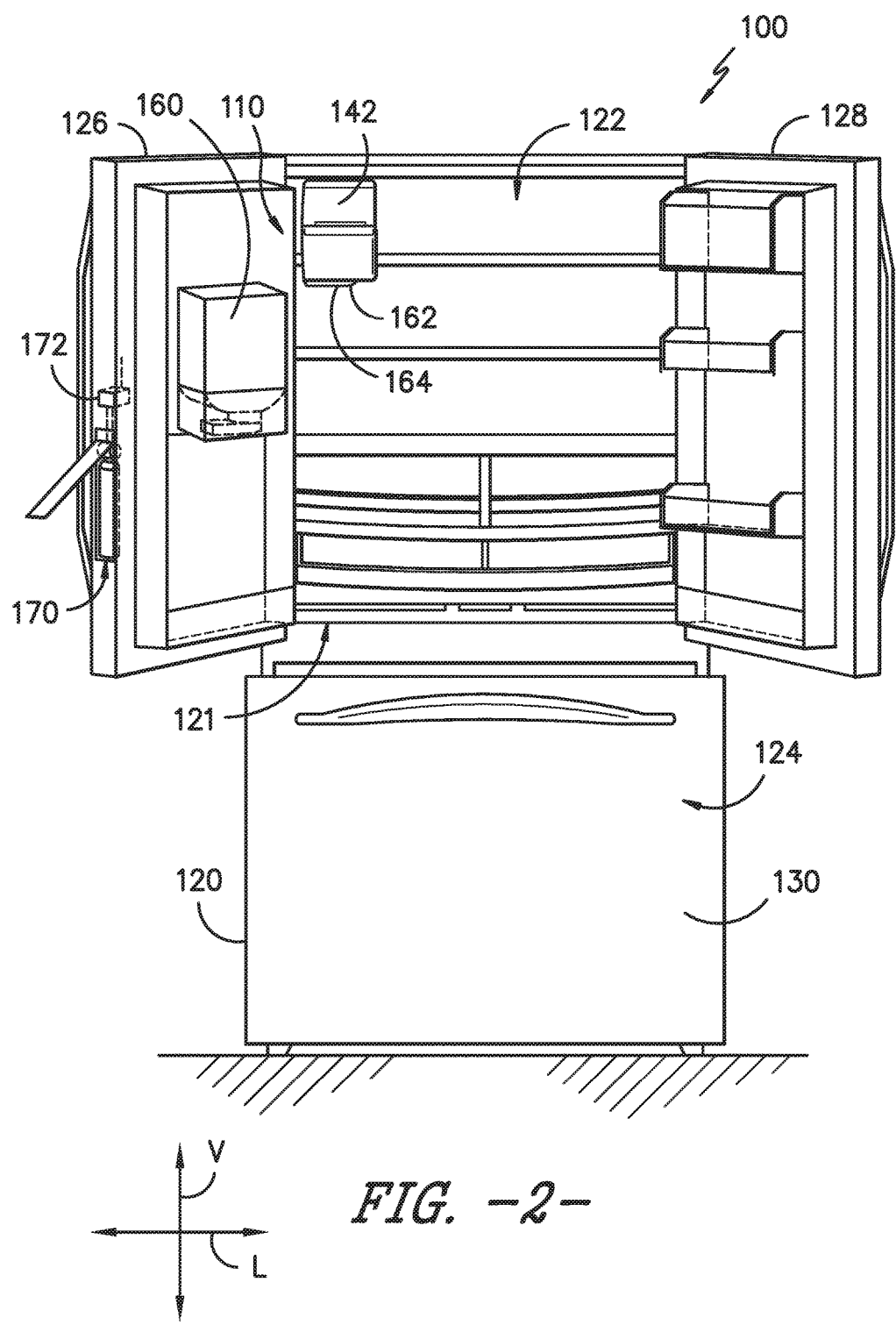
FIG. -2-

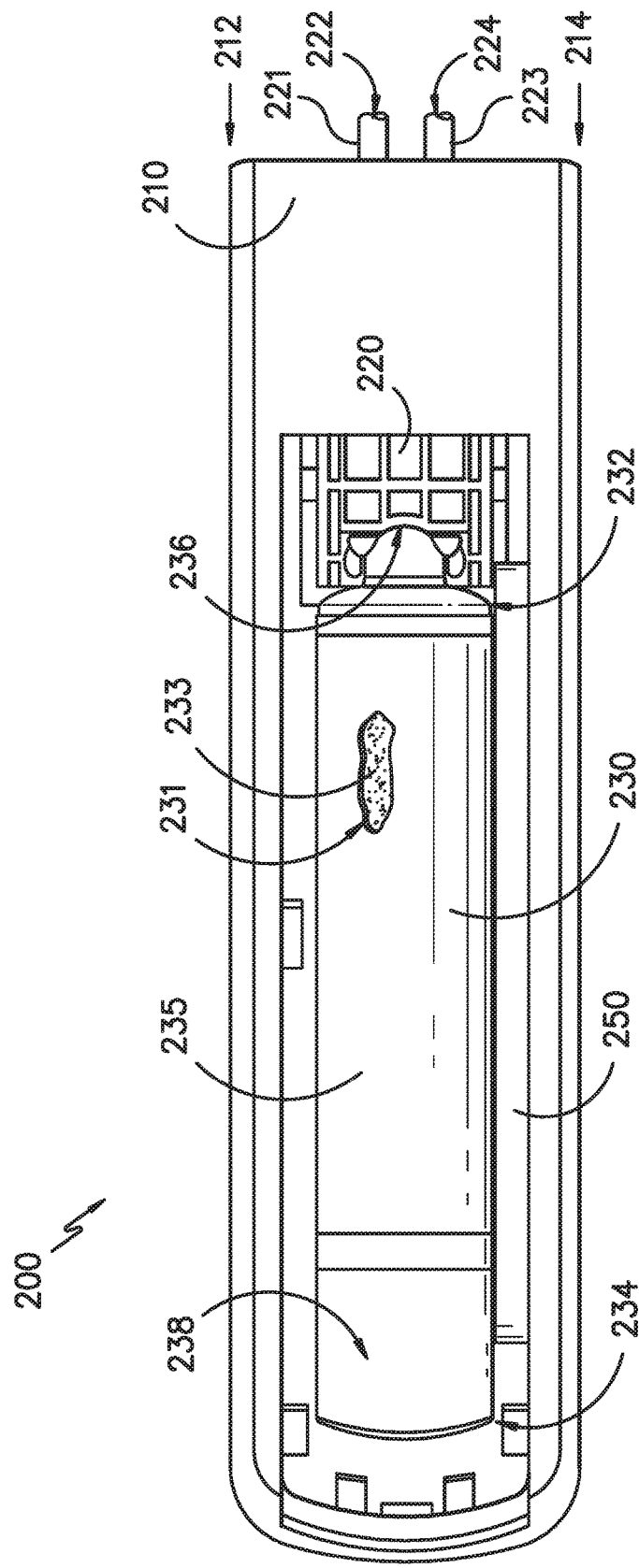
FIG. -3-

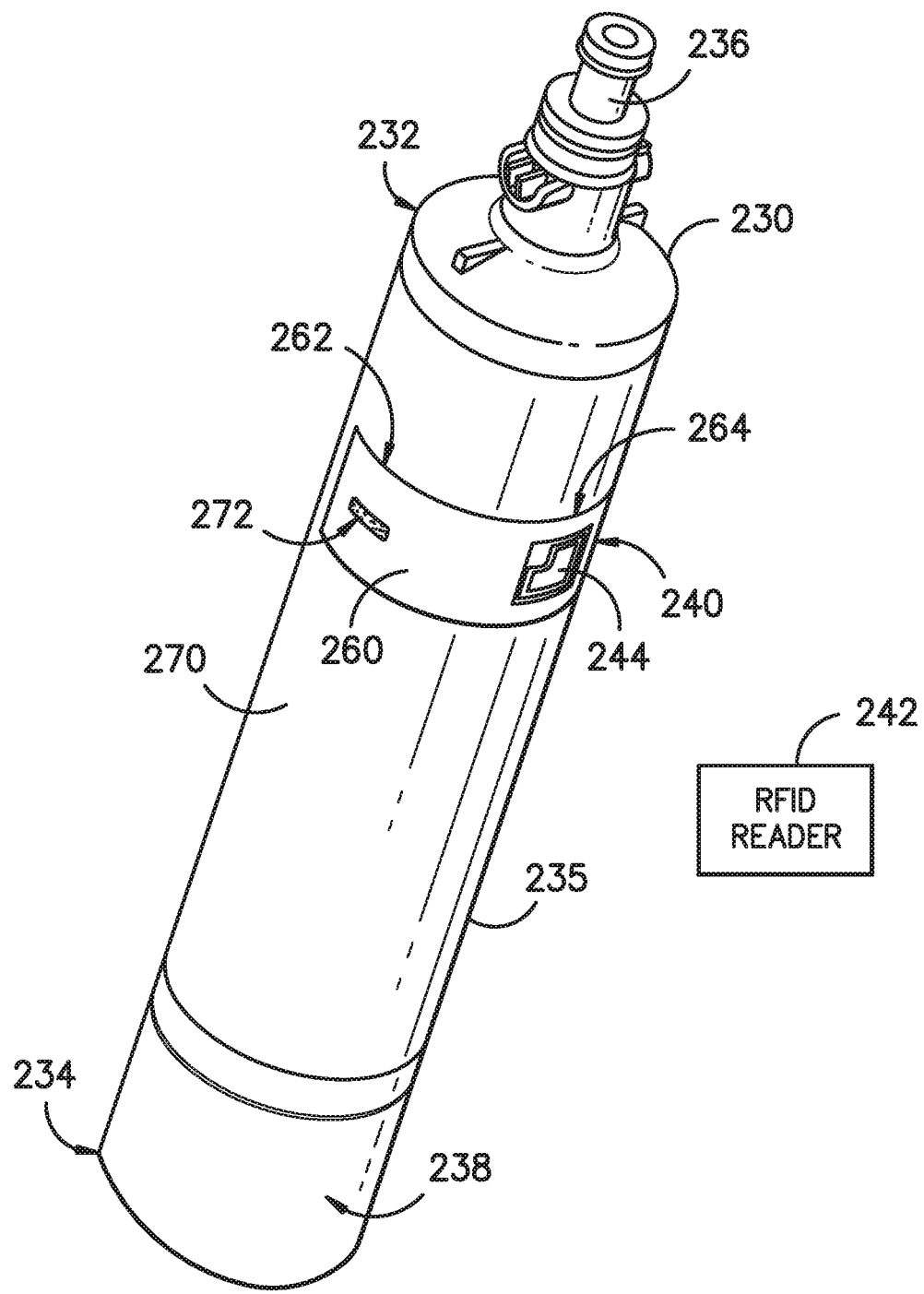
FIG. -4-

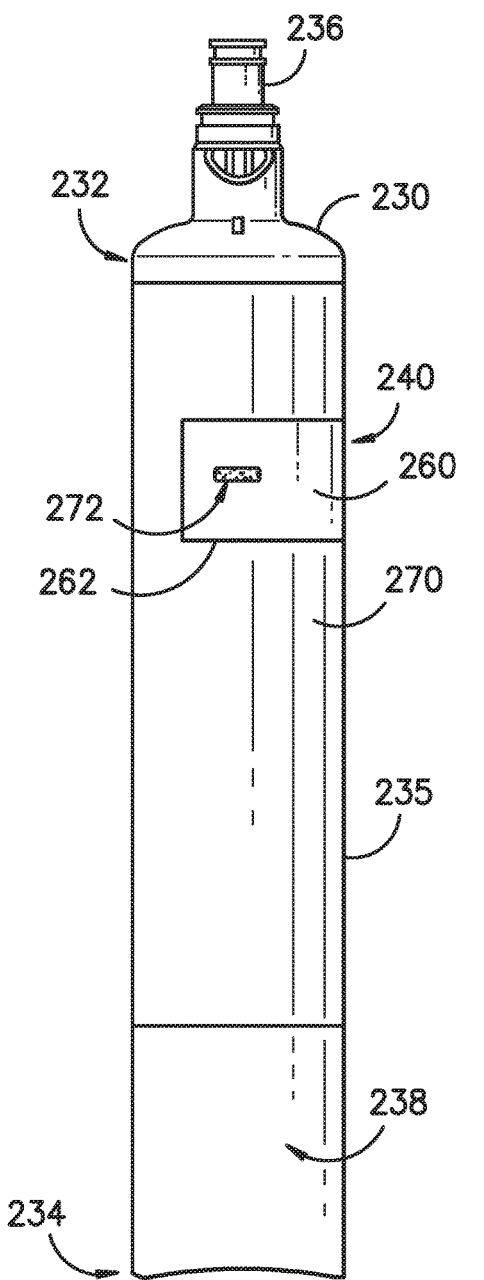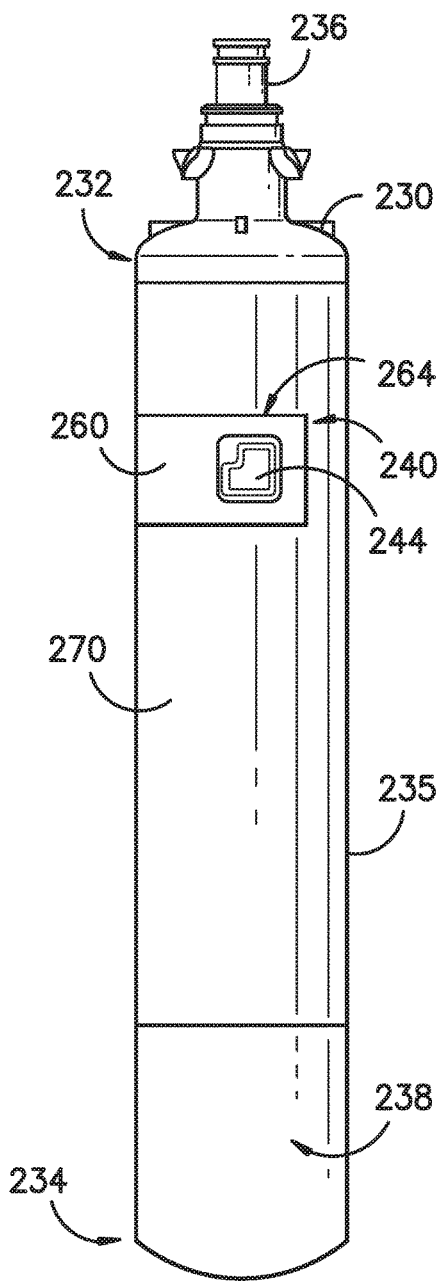
FIG. -5-   FIG. -6-

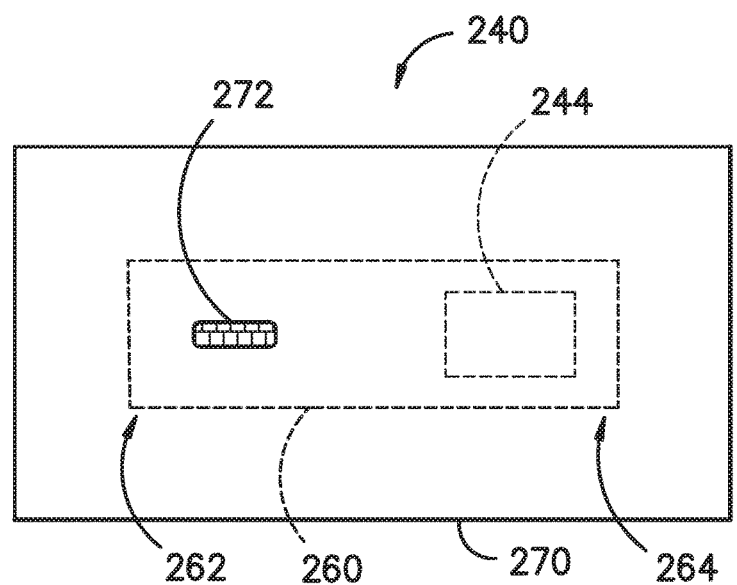
FIG. -7-

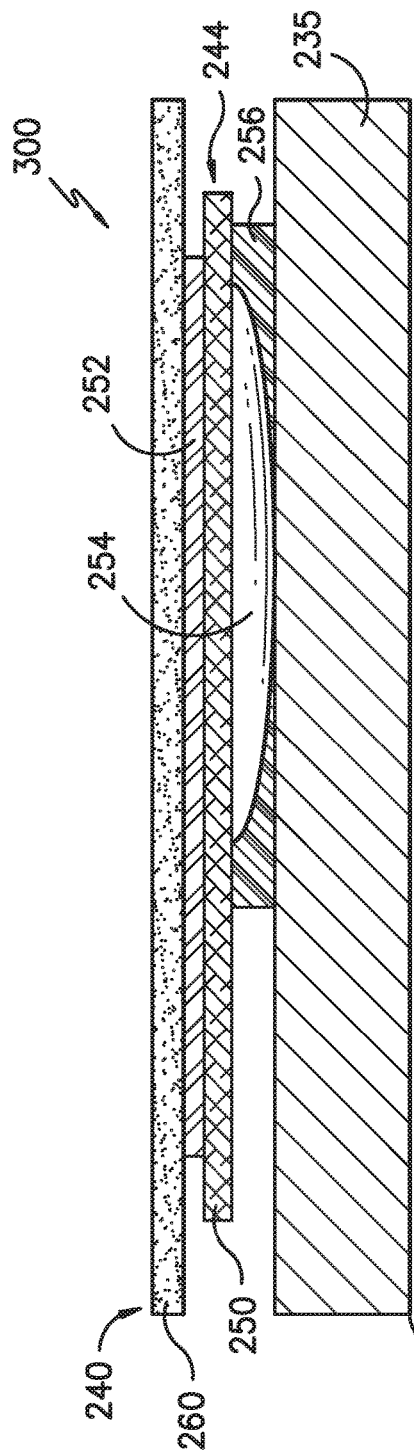
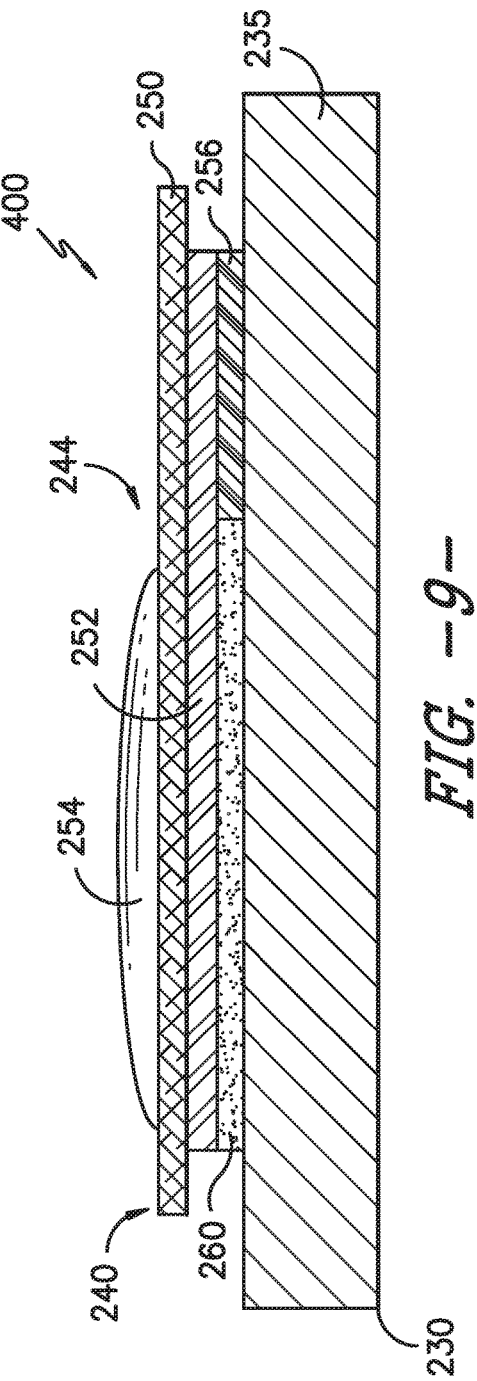

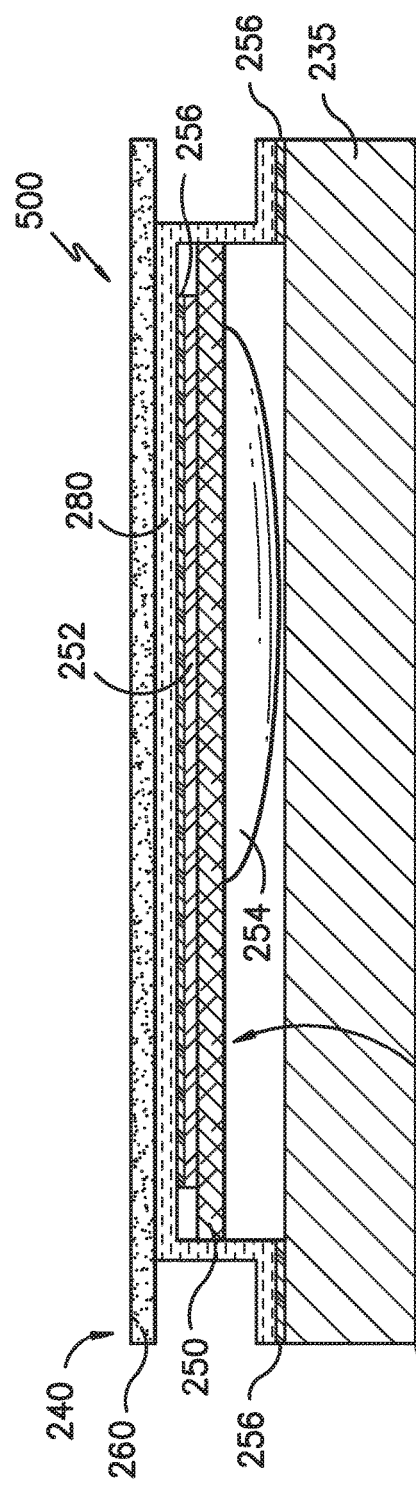
FIG. -10-
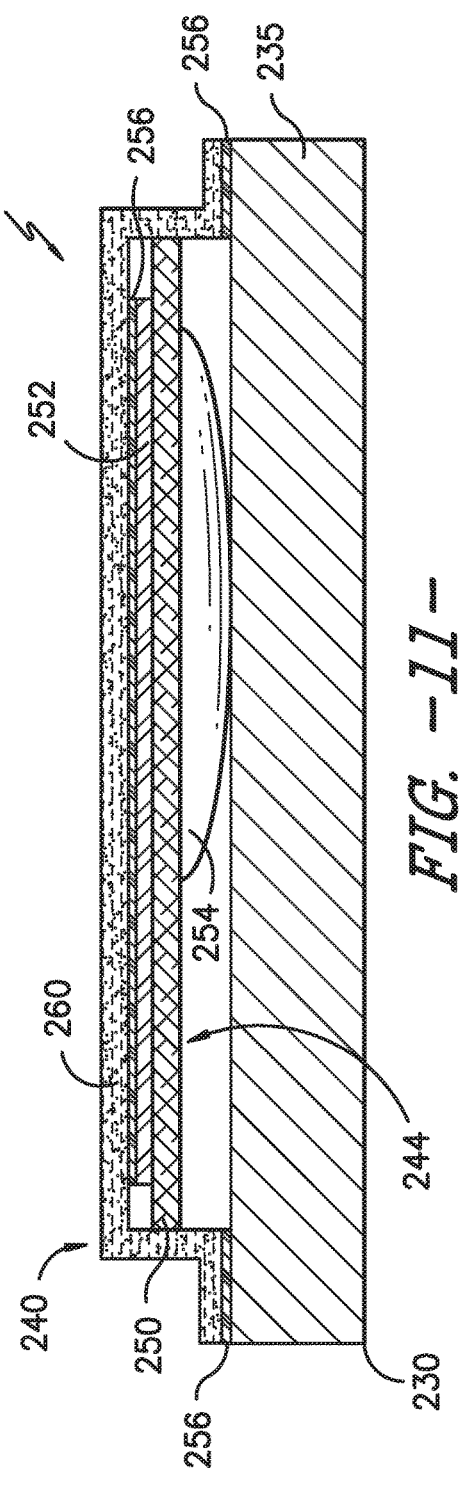
FIG. -11-

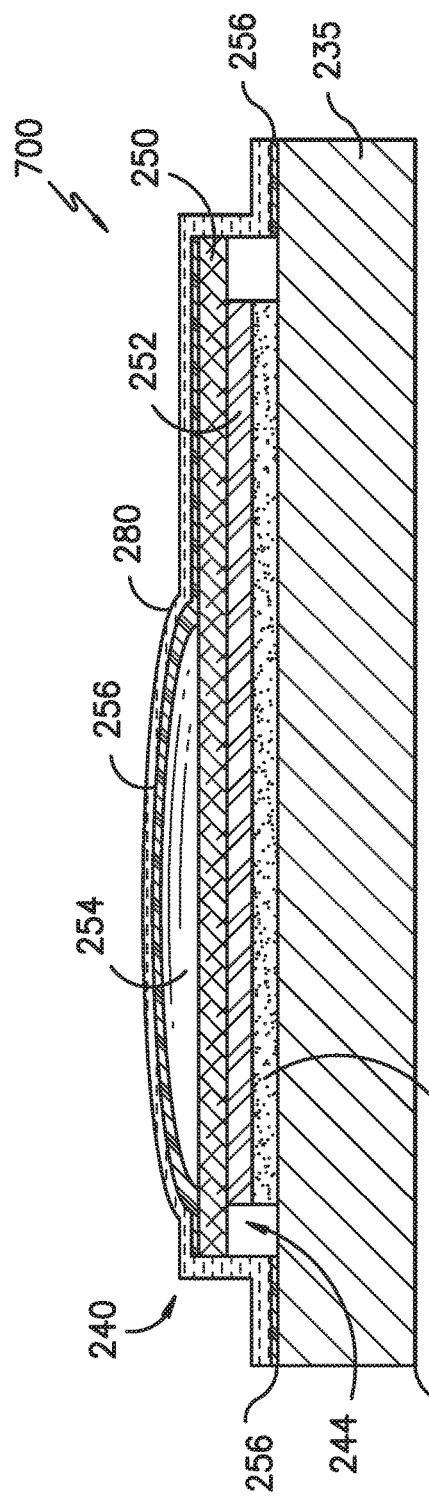
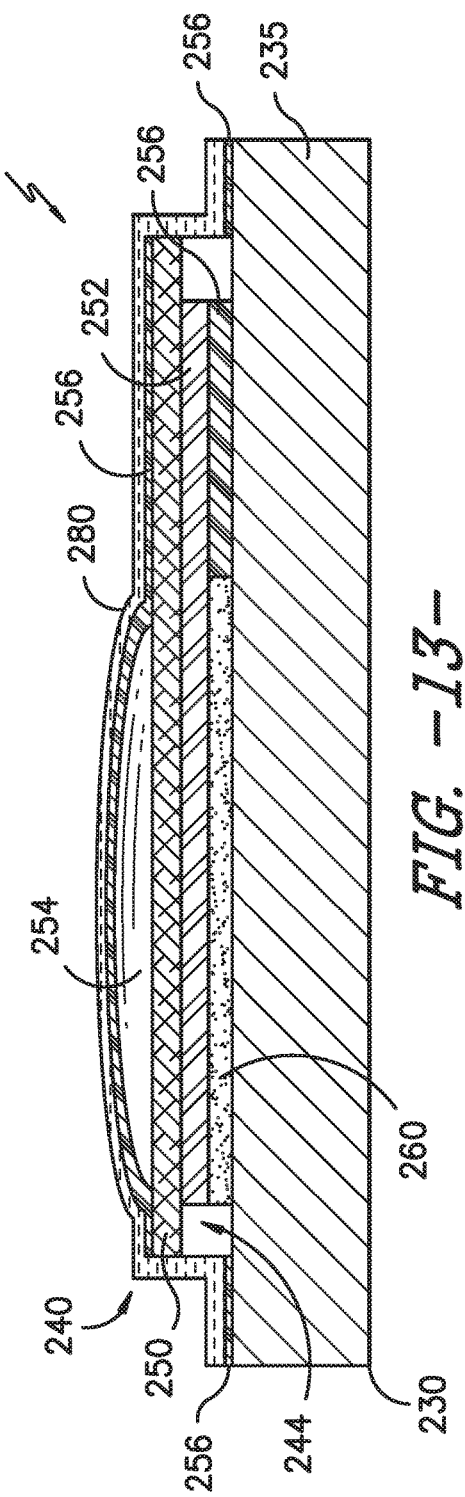
FIG. -12-
FIG. -13-

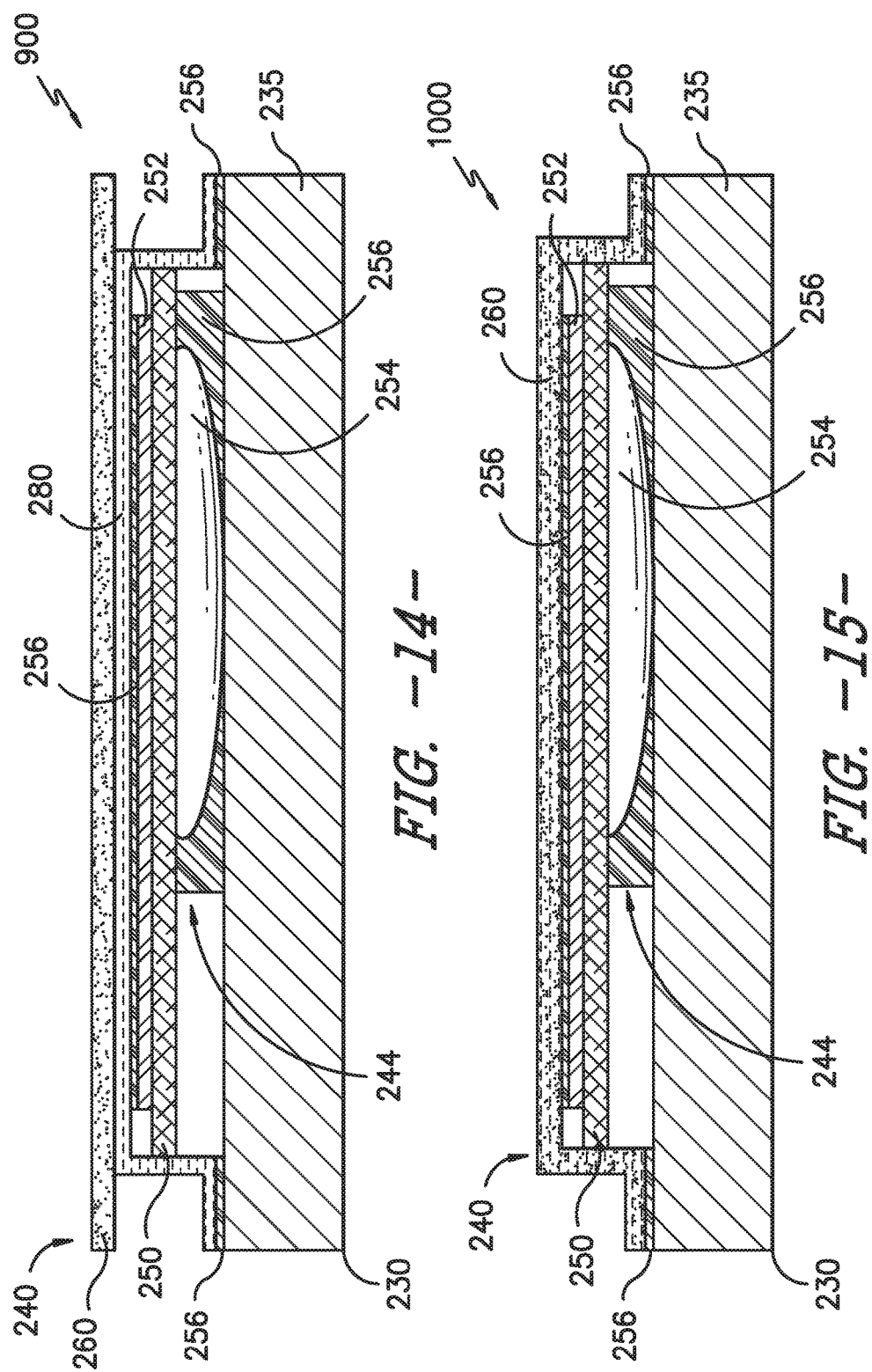

FILTER CARTRIDGE

FIELD OF THE INVENTION

The present subject matter relates generally to water filters with RFID systems.

BACKGROUND OF THE INVENTION

Certain water filter assemblies include a manifold and a filter cartridge. The manifold directs unfiltered water into the filter cartridge and filtered water out of the filter cartridge. The filter cartridge includes a filter medium, such as an activated carbon block, a pleated polymer sheet, a spun cord material, or a melt blown material. The filter medium is positioned within the filter cartridge and filters water passing therethrough.

Over time, the filter medium will lose effectiveness. For example, pores of the filter medium can become clogged or the filter medium can become saturated with contaminants. To insure that the filtering medium has not exceeded its filtering capacity, the filtering medium is preferably replaced or serviced at regular intervals regardless of its current performance. To permit replacement or servicing of the filter medium or the filter cartridge, the filter cartridge is generally removably mounted to the manifold.

Water leaks can form or develop at an interface or connection between the filter cartridge and the manifold, such as where the filter cartridge mounts to the manifold. As an example, such leaks can develop if the water filter assembly is installed incorrectly or is exposed to relatively high water pressures or freezing conditions. Such leaks can negatively affect operation of the water filter assembly and/or the refrigerator appliance and can cause damage if not prevented. Such leaks can also be difficult to detect. In particular, water filter assemblies are often positioned in relatively remote locations within refrigerator appliances such that visually monitoring the water filter assemblies for leaks can be difficult or infrequent. Similar problems can make detecting liquid water and water leaks difficult in other circumstances and locations as well.

Accordingly, a filter cartridge with features for detecting liquid, such as liquid water, would be useful. In particular, a filter cartridge with tamper resistant features for detecting liquid, such as liquid water, would be useful.

BRIEF DESCRIPTION OF THE INVENTION

The present subject matter provides a filter cartridge with a radio frequency identification tag positioned at an outer surface of a casing. The radio frequency identification tag includes an antenna and an integrated circuit. The antenna, the integrated circuit or both the antenna and the integrated circuit are fixedly connected to one or more of the casing, a water absorbent material and a fiber fabric positioned over the radio frequency identification tag on the outer surface of the casing. Additional aspects and advantages of the invention will be set forth in part in the following description, or may be apparent from the description, or may be learned through practice of the invention.

In a first example embodiment, a filter cartridge is provided. The filter cartridge includes a casing. A filter medium is positioned within the casing. A radio frequency identification tag is positioned at an outer surface of the casing. The radio frequency identification tag includes an antenna and an integrated circuit. A water absorbent material is positioned proximate the radio frequency identification tag such that signal communication of the radio frequency identification tag is disrupted when liquid water is disposed within the water absorbent material. A water impermeable material is positioned over the water absorbent material and the radio frequency identification tag on the outer surface of the casing. The antenna, the integrated circuit or both the antenna and the integrated circuit are adhered to one or more of the casing, the water absorbent material and a fiber fabric positioned over the radio frequency identification tag on the outer surface of the casing.

In a second example embodiment, a filter cartridge is provided. The filter cartridge includes a casing. A filter medium is positioned within the casing. A radio frequency identification tag is positioned at an outer surface of the casing. The radio frequency identification tag includes an antenna and an integrated circuit. A water absorbent material is positioned proximate the radio frequency identification tag such that signal communication of the radio frequency identification tag is disrupted when liquid water is disposed within the water absorbent material. A water impermeable material is positioned over the water absorbent material and the radio frequency identification tag on the outer surface of the casing. The antenna, the integrated circuit or both the antenna and the integrated circuit are fixedly connected to one or more of the casing and the water absorbent material.

In a third example embodiment, a filter cartridge is provided. The filter cartridge includes a casing. A filter medium is positioned within the casing. A radio frequency identification tag is positioned at an outer surface of the casing. The radio frequency identification tag includes an antenna and an integrated circuit. A fiber reinforced water absorbent material is positioned proximate the radio frequency identification tag such that signal communication of the radio frequency identification tag is disrupted when liquid water is disposed within the fiber reinforced water absorbent material. A water impermeable material is positioned over the fiber reinforced water absorbent material and the radio frequency identification tag on the outer surface of the casing. The antenna, the integrated circuit or both the antenna and the integrated circuit are fixedly connected to the fiber reinforced water absorbent material.

In a fourth example embodiment, a filter cartridge is provided. The filter cartridge includes a casing. A filter medium is positioned within the casing. A radio frequency identification tag is positioned at an outer surface of the casing. The radio frequency identification tag includes an antenna and an integrated circuit. A water absorbent material is positioned proximate the radio frequency identification tag such that signal communication of the radio frequency identification tag is disrupted when liquid water is disposed within the water absorbent material. A fiber fabric is positioned over the radio frequency identification tag on the outer surface of the casing. A water impermeable material is positioned over the water absorbent material and the radio frequency identification tag on the outer surface of the casing. The antenna, the integrated circuit or both the antenna and the integrated circuit are fixedly connected to the fiber fabric.

In a fifth example embodiment, a filter cartridge is provided. The filter cartridge includes a casing. A filter medium is positioned within the casing. A radio frequency identification tag is positioned at an outer surface of the casing. The radio frequency identification tag includes an antenna and an integrated circuit. The antenna, the integrated circuit or both the antenna and the integrated circuit are adhered to the casing.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

FIG. 1 provides a front, elevation view of a refrigerator appliance according to an example embodiment of the present subject matter with refrigerator doors of the example refrigerator appliance shown in a closed position.

FIG. 2 provides a front, elevation view of the example refrigerator appliance of FIG. 1 with refrigerator doors of the example refrigerator appliance shown in an open position.

FIG. 3 provides a front, elevation view of a water filter assembly according to an example embodiment of the present subject matter.

FIG. 4 provides a perspective view of a filter cartridge of the example water filter assembly of FIG. 3.

FIGS. 5 and 6 provide elevation views of the filter cartridge of FIG. 4.

FIG. 7 provides a plan view of certain components of an example system for detecting liquid water.

FIGS. 8 through 15 provide various section views of the example system of FIG. 7 with respective arrangements for fixedly connecting a component the example system to the filter cartridge of FIG. 4.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

FIG. 1 provides a front, elevation view of a refrigerator appliance 100 according to an example embodiment of the present subject matter. FIG. 2 provides a front, elevation view of refrigerator appliance 100 with refrigerator doors 126 and 128 of refrigerator appliance 100 shown in an open position to reveal a fresh food chamber 122 of refrigerator appliance 100. Refrigerator appliance 100 defines a vertical direction V, and a lateral direction L. The vertical direction V and lateral direction L are perpendicular. Refrigerator appliance 100 extends between an upper portion 101 and a lower portion 102 along the vertical direction V. Refrigerator appliance 100 also extends between a first side portion 105 and a second side portion 106 along the lateral direction L.

Refrigerator appliance 100 includes a cabinet 120 that defines chilled chambers for receipt of food items for storage. In particular, refrigerator appliance 100 defines fresh food chamber 122 at upper portion 101 of refrigerator appliance 100 and a freezer chamber 124 arranged below fresh food chamber 122 on the vertical direction V, e.g., at lower portion 102 of refrigerator appliance 100. As such, refrigerator appliance 100 is generally referred to as a bottom mount refrigerator appliance. However, using the teachings disclosed herein, one of skill in the art will understand that the present subject matter may be used with other types of refrigerator appliances (e.g., side-by-side style or top mount style) or a freezer appliance as well. Consequently, the description set forth herein is for illustrative purposes only and is not intended to limit the present subject matter to any particular chilled chamber arrangement.

Refrigerator doors 126 and 128 are rotatably hinged to an edge of cabinet 120 for accessing fresh food chamber 122. In particular, cabinet 120 defines an opening 121. Opening 121 of cabinet 120 permits access to fresh food chamber 122 of cabinet 120. Refrigerator doors 126 and 128 are positioned at opening 121 of cabinet 120 and permit selective access to fresh food chamber 122 of cabinet 120 through opening 121 of cabinet 120, e.g., by rotating between the open and closed positions. A freezer door 130 is arranged below refrigerator doors 126 and 128 for accessing freezer chamber 124. Freezer door 130 is coupled to a freezer drawer (not shown) slidably mounted within freezer chamber 124.

Refrigerator appliance 100 also includes a dispensing assembly 110 for dispensing water and/or ice. Dispensing assembly 110 includes a dispenser 114 positioned on or mounted to an exterior portion of refrigerator appliance 100, e.g., on refrigerator door 126. Dispenser 114 includes a discharging outlet 134 for accessing ice and water. A sensor 132, such as an ultrasonic sensor, is mounted below discharging outlet 134 for operating dispenser 114. In alternative example embodiments, any suitable actuator may be used to operate dispenser 114. For example, dispenser 114 can include a paddle or button rather than sensor 132. A user interface panel 136 is provided for controlling the mode of operation. For example, user interface panel 136 includes a water dispensing button (not labeled) and an ice-dispensing button (not labeled) for selecting a desired mode of operation such as crushed or non-crushed ice.

Discharging outlet 134 and sensor 132 are an external part of dispenser 114 and are mounted in a dispenser recess 138 defined in an outside surface of refrigerator door 126. Dispenser recess 138 is positioned at a predetermined elevation convenient for a user to access ice or water and enabling the user to access ice without the need to bend-over and without the need to access freezer chamber 124. In the example embodiment, dispenser recess 138 is positioned at a level that approximates the chest level of a user.

Turning now to FIG. 2, certain components of dispensing assembly 110 are illustrated. Dispensing assembly 110 includes an insulated housing 142 mounted within fresh food chamber 122. Due to the insulation which encloses insulated housing 142, the temperature within insulated housing 142 can be maintained at levels different from the ambient temperature in the surrounding fresh food chamber 122.

Insulated housing 142 is constructed and arranged to operate at a temperature that facilitates producing and storing ice. More particularly, insulated housing 142 contains an ice maker (not shown) for creating ice and feeding the same to a container 160 that is mounted on refrigerator door 126. As illustrated in FIG. 2, container 160 is placed at a vertical position on refrigerator door 126 that will allow for the receipt of ice from a discharge opening 162 located along a bottom edge 164 of insulated housing 142. As refrigerator door 126 is closed or opened, container 160 is moved in and out of position under insulated housing 142.

Refrigerator appliance 100 also includes a water filter assembly 170. Water filter assembly 170 can filter water from a water supply (not shown), such as a municipal water source or a well. Water filter assembly 170 can remove contaminants and other undesirable substances from water passing therethrough. As used herein, the term "water" includes purified water and solutions or mixtures containing water and, e.g., elements (such as calcium, chlorine, and fluorine), salts, bacteria, nitrates, organics, and other chemical compounds or substances.

Water filter assembly 170 is mounted to cabinet 120. In particular, water filter assembly 170 is mounted to refrigerator door 126 in the example embodiment shown in FIG. 2. However, it should be understood that water filter assembly 170 can be positioned at any other suitable location within refrigerator appliance 100 in alternative example embodiments. For example, water filter assembly 170 may be mounted to refrigerator door 128, to cabinet 120 within fresh food chamber 122, or to cabinet 120 below freezer chamber 124 in alternative example embodiments. Thus, the position of water filter assembly 170 shown in FIG. 2 is not intended to limit the present subject matter in any aspect and is provided by way of example only.

Refrigerator appliance 100 also includes a valve 172 as schematically shown in FIG. 2. Valve 172 is configured for regulating a flow of water to water filter assembly 170. In particular, valve 172 can selectively shift between a closed position and an open position. Valve 172 permits the flow of water to water filter assembly 170 in the open position. Thus, with valve 172 in the open position, water for filtering is supplied to water filter assembly 170. Conversely, valve 172 obstructs or blocks the flow of water to water filter assembly 170 in the closed position. Thus, with valve 172 in the closed position, water for filtering is not supplied to water filter assembly 170 or is supplied to water filter assembly 170 in an insubstantial volume. In such a manner, valve 172 can regulate the flow of water to water filter assembly 170 by shifting between the open and closed positions.

FIG. 3 provides a front elevation view of a water filter assembly 200 according to an example embodiment of the present subject matter. Water filter assembly 200 can be used in any suitable appliance. For example, water filter assembly 200 may be used in refrigerator appliance 100 (FIG. 2) as water filter assembly 170 (FIG. 2). As discussed in greater detail below, water filter assembly 200 is configured for filtering water passing therethrough. In such a manner, water filter assembly 200 can provide filtered water to various components of refrigerator appliance 100, such as dispensing assembly 110 or the ice maker (not shown) within insulated housing 142. Water filter assembly 200 may also be used to filter water at any other suitable location. For example, water filter assembly 200 may be utilized as a point-of-entry water filter for a building or residence. As another example, water filter assembly 200 may be utilized as a point-of-use water filter for a faucet, a water fountain, etc.

As may be seen in FIG. 3, water filter assembly 200 includes a housing 210. Housing 210 extends between a top portion 212 and a bottom portion 214, e.g., along the vertical direction V. As an example, housing 210 can be mounted to any suitable portion of refrigerator appliance 100 in order to mount water filter assembly 200 to refrigerator appliance 100. For example, housing 210 may be mounted to refrigerator door 126 or cabinet 120. In particular, housing 210 may be encased within or engage insulating foam (not shown) of cabinet 120 to mount water filter assembly 200 to refrigerator appliance 100. As another example, housing 210 may be mounted to a wall of building or residence, e.g., when water filter assembly 200 is utilized as a point-of-entry water filter.

Water filter assembly 200 also includes a manifold 220. Manifold 220 is mounted to housing 210. Manifold 220 is configured for receiving unfiltered water and directing filtered water out of water filter assembly 200. In particular, manifold 220 includes an inlet conduit 221 that defines an inlet 222. Inlet 222 receives unfiltered water, e.g., from a water source (not shown) such as a municipal water supply or a well. Manifold 220 also includes an outlet conduit 223 that defines an outlet 224. Outlet 224 directs filtered water out of water filter assembly 200. Thus, manifold 220 receives unfiltered water at inlet 222. Such unfiltered water passes through water filter assembly 200 and exits manifold 220 at outlet 224 as filtered water.

As shown in FIG. 3, water filter assembly 200 includes a filter canister or filter cartridge 230 for filtering unfiltered water received at inlet 222 of manifold 220. Thus, filter cartridge 230 filters water passing through water filter assembly 200. Filter cartridge 230 extends between a first end portion 232 and a second end portion 234, e.g., along the lateral direction L. A connection 236 of filter cartridge 230 is positioned at or proximate first end portion 232 of filter cartridge 230. Connection 236 of filter cartridge 230 is configured for engaging manifold 220, e.g., in order to removably mount filter cartridge 230 to manifold 220.

Connection 236 of filter cartridge 230 also places filter cartridge 230 in fluid communication with manifold 220 when filter cartridge 230 is mounted to manifold 220. Thus, filter cartridge 230 can receive unfiltered water from inlet 222 of manifold 220 at connection 236 and direct such unfiltered water into a chamber 231 defined by a casing 235 of filter cartridge 230 when filter cartridge 230 is mounted to manifold 220. Water within chamber 231 can pass through a filtering medium 233 positioned within chamber 231 and can exit chamber 231 as filtered water. In particular, connection 236 of filter cartridge 230 can direct filtered water out of chamber 231 to outlet 224 of manifold 220 when filter cartridge 230 is mounted to manifold 220. In such a manner, filtering medium 233 of filter cartridge 230 can filter a flow of water through water filter assembly 200. Such filtering can improve taste and/or safety of water.

Filtering medium 233 can include any suitable mechanism for filtering water within water filter assembly 200. For example, filtering medium 233 may include an activated carbon block, a reverse osmosis membrane, a pleated polymer or cellulose sheet, or a melt blown or spun cord medium. As used herein, the term "unfiltered" describes water that is not filtered relative to filtering medium 233. However, water filter assembly 200 may include additional filters that filter water entering chamber 231. Thus, "unfiltered" may be filtered relative to other filters but not filtering medium 233.

Filtering medium 233 of filter cartridge 230 can lose efficacy over time. Thus, a user can replace filter cartridge and/or filtering medium 233 of filter cartridge 230 at regular intervals or after a certain volume of water has passed through filter cartridge 230. To replace filter cartridge 230 and/or filtering medium 233 of filter cartridge 230, the user can remove or disconnect filter cartridge 230 from manifold 220 and insert or mount a new filter cartridge 230 or filtering medium 233 of filter cartridge 230.

Water filter assembly 200 can be exposed to a variety of conditions within that can negatively affect performance of water filter assembly 200. For example, high water pressure at inlet 222 of manifold 220 and/or connection 236 of filter cartridge 230 or exposing water filter assembly 200 to freezing conditions can negatively affect performance of water filter assembly 200. Such conditions can cause water filter assembly 200 to leak, e.g., at connection 236 of filter cartridge 230. Such conditions can also cause water filter assembly 200 to deform or crack. As discussed in greater detail below, water filter assembly 200 includes features for detecting such malfunctions of water filter assembly 200.

FIG. 4 provides a perspective view of filter cartridge 230 of water filter assembly 200. FIGS. 5 and 6 provide elevation views of filter cartridge 230. As may be seen in FIGS. 4, 5 and 6, water filter assembly 200 includes a system 240 for detecting liquid water. It should be understood that system 240 can be used to detect liquid water and/or water leaks in any other suitable setup or arrangement in alternative example embodiments. Thus, while described in the context of water filter assembly 200, system 240 may be used to detect water leaks from any suitable container, vessel, pipe or conduit or to detect liquid water in the container, vessel, pipe or conduit or on the surface in alternative example embodiments.

As may be seen in FIG. 4, system 240 includes a radio frequency identification reader or RFID reader 242 (shown schematically). System 240 also includes a radio frequency identification tag or RFID tag 244, e.g., positioned on casing 235 opposite filtering medium 233. RFID reader 242 is configured for receiving a signal from RFID tag 244. Thus, RFID reader 242 and RFID tag 244 can be in signal communication with each other. For example, RFID reader 242 and RFID tag 244 may be in signal communication with each other as described in U.S. Pat. No. 9,366,388 entitled "A Refrigerator Appliance and A Method For Monitoring A Water Filter Assembly Within The Same" and/or U.S. Pat. No. 9,274,020 entitled "A System And A Method For Detecting Liquid Water," both of which are incorporated by reference herein in their entireties.

In certain example embodiments, RFID tag 244 is a passive RFID tag. Thus, RFID reader 242 can receive a radio signal from RFID tag 244 in response to a query or request signal from RFID reader 242. In particular, RFID tag 244 can generate or transmit the response radio signal utilizing energy transmitted, e.g., wirelessly, to RFID tag 244 from RFID reader 242 via the query or request signal from RFID reader 242. Thus, RFID tag 244 need not include a battery or other power source in order to generate or transmit the response radio signal. In other example embodiments, RFID tag 244 is an active RFID tag and includes a battery or is connected to a suitable power source. Thus, RFID tag 244 can continuously or intermittently generate or transmit a signal that RFID reader 242 can receive. RFID reader 242 and RFID tag 244 can have any other suitable setup or configuration for placing RFID reader 242 and RFID tag 244 in signal communication with each other. Thus, RFID reader 242 may be passive or active, and RFID tag 244 may be passive or active depending upon the desired setup of system 240.

Signal communication between RFID reader 242 and RFID tag 244 is affected by a variety of factors. For example, signal communication between RFID reader 242 and RFID tag 244 can be limited or terminated if a gap between RFID reader 242 and RFID tag 244 is increased. RFID reader 242 and RFID tag 244 can also be tuned such that signal communication between RFID reader 242 and RFID tag 244 is established with a particular transmission medium, such as air, disposed between RFID reader 242 and RFID tag 244, e.g., within the gap between RFID reader 242 and RFID tag 244. Thus, the signal communication between RFID reader 242 and RFID tag 244 can be disrupted or terminated if the transmission medium changes and another material is positioned between RFID reader 242 and RFID tag 244. For example, if water is positioned between RFID reader 242 and RFID tag 244, the signal communication between RFID reader 242 and RFID tag 244 can be terminated or disrupted. In particular, liquid water can absorb radio waves and thereby terminate or disrupt signal communication between RFID reader 242 and RFID tag 244. Liquid water can also affect transmission and reception of radio waves by antennas of RFID reader 242 and/or RFID tag 244. As discussed in greater detail below, when signal communication between RFID reader 242 and RFID tag 244 is disrupted, lost or terminated, it can be inferred that liquid water is disposed between RFID reader 242 and RFID tag 244 (e.g., that liquid water is disposed within the gap between RFID reader 242 and RFID tag 244). For example, when signal communication between RFID reader 242 and RFID tag 244 is interrupted, it can be inferred that water filter assembly 200 is leaking or otherwise malfunctioning.

System 240 also include features for wicking liquid from a liquid collection location to RFID tag 244. Thus, RFID tag 244 may detect liquid water and/or water leaks despite RFID tag 244 being spaced apart or remotely located from the liquid collection location. As an example, RFID tag 244 may be positioned above a pool of liquid, e.g., along the vertical direction V, formed by liquid leaking from filter cartridge 230 and/or connection 236 of filter cartridge 230 and manifold 220. The liquid can be wicked upwardly to RFID tag 244 in order to disrupt or terminate the signal communication between RFID reader 242 and RFID tag 244.

As may be seen in FIG. 6, system 240 includes a hydroscopic or absorbent material 260. Absorbent material 260 extends between a first end portion 262 and a second end portion 264, e.g., along the vertical direction V. First and second end portions 262 and 264 of absorbent material 260 are spaced apart from each other, e.g., along the vertical direction V and/or circumferentially on filter cartridge 230. Thus, first and second end portions 262 and 264 of absorbent material 260 may be positioned at separate locations, and absorbent material 260 may wick or otherwise transfer liquid between the first and second end portions 262 and 264 of absorbent material 260. As an example, first end portion 262 of absorbent material 260 may be positioned at a liquid collection location. Conversely, second end portion 264 of absorbent material 260 may be positioned at or over RFID tag 244. Thus, second end portion 264 of absorbent material 260 and RFID tag 244 may be spaced apart from the liquid collection location, and absorbent material 260 may wick or otherwise transfer liquid from the liquid collection location to the RFID tag 244. In such a manner, absorbent material 260 may assist with permitting RFID tag 244 to be positioned remotely relative to the liquid collection location, and, thereby, permit detection of liquid with system 240 at locations where RFID tag 244 cannot be directly positioned.

Absorbent material 260 may be any suitable absorbent material. For example, absorbent material 260 may be or include cellulose foam, paper or synthetic foam. In addition, an electrolyte may be disposed within absorbent material 260. Thus, absorbent material 260 may be doped with the electrolyte. Any suitable electrolyte may be disposed within absorbent material 260. For example, a water soluble electrolyte, such as sodium bicarbonate, sodium chloride or potassium sulfate, may be disposed within absorbent material 260. It will be understood that absorbent material 260 need not be a single, continuous piece of material. Thus, e.g., absorbent material 260 may be constructed of or with a plurality of absorbent pieces positioned adjacent each other.

As discussed above, RFID tag 244 may be inoperable or signal communication between RFID tag 244 and RFID reader 242 may be diminished, e.g., if liquid is disposed within absorbent material 260 at second end portion 264 of absorbent material 260. For example, liquid within absorbent material 260 at second end portion 264 of absorbent material 260 may short out the antenna of RFID tag 244. As another example, a resistance of absorbent material 260 can decrease (e.g., due to the electrolyte therein dissolving) thereby putting a load on the antenna of RFID tag 244. As the resistance drops, the load can increase until the load drains sufficient power from RFID tag 244 such that RFID tag 244 is disabled or deactivated and signal communication between RFID reader 242 and RFID tag 244 is disrupted or terminated. Further, when absorbent material 260 is wet, e.g., such that the electrolyte within absorbent material 260 is dissolved, the capacitance of the antenna of RFID tag 244 may be a second capacitance value. The second capacitance value can be selected such that the signal communication between RFID reader 242 and RFID tag 244 is disrupted or terminated due to the associated change in the resonant frequency of RFID tag 244.

As may be seen in FIG. 4, system 240 also includes an impermeable material 270. Impermeable material 270 may be positioned over RFID tag 244 and/or absorbent material 260. As an example, impermeable material 270 may be mounted to filter cartridge 230 at outer surface 238 of filter cartridge 230. Thus, impermeable material 270 may assist with mounting or securing RFID tag 244 and/or absorbent material 260 to filter cartridge 230.

Impermeable material 270 defines a passage 272 therethrough. Passage 272 permits liquid to flow through impermeable material 270, e.g., to absorbent material 260 disposed below impermeable material 270. As an example, passage 272 of impermeable material 270 may be positioned at or adjacent the liquid collection location, and first end portion 262 of absorbent material 260 may be positioned at or adjacent passage 272 of impermeable material 270. Thus, impermeable material 270 may be positioned between the liquid collection location and absorbent material 260, and passage 272 may permit liquid to flow through impermeable material 270 to absorbent material 260. In particular, absorbent material 260 may be configured or positioned for wicking liquid from passage 272 of impermeable material 270 at first end portion 262 of absorbent material 260 to second end portion 264 of absorbent material 260 and RFID tag 244. Thus, impermeable material 270 may assist with hindering or preventing absorbent material 260 from collecting or absorbing liquid from locations other than the liquid collection location. In particular, passage 272 may be the only location at which liquid can pass through impermeable material 270 to absorbent material 260. Thus, impermeable material 270 may seal or encase RFID tag 244 and absorbent material 260 on casing 235 of filter cartridge 230 such that RFID tag 244 only deactivates in response to liquid passing through impermeable material 270 to absorbent material 260.

Impermeable material 270 may be constructed of or with any suitable impermeable material 270. For example, impermeable material 270 may be constructed of or with a material that is impermeable to the liquid being detected by system 240. In certain example embodiments, impermeable material 270 may be, e.g., flexible, plastic film or layer. In addition, impermeable material 270 may further include an adhesive, such as a pressure sensitive adhesive, disposed on the plastic film. Thus, impermeable material 270 may act as a sticker or tape to assist with mounting absorbent material 260 and RFID tag 244 to a surface. In such a manner, system 240 may be easily mountable at or adjacent a liquid collection location.

As discussed in greater detail below, system 240 also includes features for assisting with fixedly connecting components of system 240 to one or more of casing 235, absorbent material 260 and a fiber fabric 270. Thus, system 240 may be reliably and/or permanently attached to filter cartridge 230. In such a manner, performance of filter cartridge 230 may be improved, and/or defacement of filter cartridge 230 may be limited. As may be seen in FIGS. 8 through 15, RFID tag 244 includes a substrate 250, an antenna 252 and an integrated circuit 254. Antenna 252, integrated circuit 254 or both antenna 252 and integrated circuit 254 may be fixedly connected to one or more of casing 235, absorbent material 260 and fiber fabric 270. As used herein, the term "fixedly connected" means permanently or non-removably connected such that antenna 252 and/or integrated circuit 254 detach from substrate 250 and RFID tag 244 is rendered inoperable if system 240 is removed from filter cartridge. Thus, RFID tag 244 may be tamperproof or tamper resistant in order to limit undesirable modification of filter cartridge 230.

FIGS. 8 through 15 provide various section views of system 240 with respective arrangements for fixedly connecting antenna 252, integrated circuit 254 or both antenna 252 and integrated circuit 254 to one or more of casing 235, absorbent material 260 and fiber fabric 270. It will be understood that the arrangements for fixedly connecting components of system 240 to one or more of casing 235, absorbent material 260 and fiber fabric 270 shown in FIGS. 8 through 15 are provided by way of example only and that other arrangements and combination of arrangements may be provided in alternative example embodiments. Each example arrangement for fixedly connecting antenna 252, integrated circuit 254 or both antenna 252 and integrated circuit 254 to one or more of casing 235, absorbent material 260 and fiber fabric 270 is discussed in greater detail below.

FIG. 8 provides a section view of a first example arrangement 300 of system 240. In FIG. 8, integrated circuit 254 is adhered to casing 235, and adhesive 256 extends between integrated circuit 254 and casing 235. Thus, e.g., integrated circuit 254 may detach from substrate 250, e.g., and remain attached to casing 235, if RFID is removed from filter cartridge 230. Integrated circuit 254 may be positioned opposite antenna 252 on substrate 250. Absorbent material 260 may be positioned on and/or contact antenna 252. Thus, liquid water in absorbent material 260 may deactivate antenna 252, as discussed in greater detail above. Impermeable material 270 may be positioned over or on absorbent material 260, e.g., opposite absorbent material 260.

FIG. 9 provides a section view of a second example arrangement 400 of system 240. In FIG. 9, antenna 252 is adhered to casing 235, and adhesive 256 extends between antenna 252 and casing 235. Thus, e.g., antenna 252 may detach from substrate 250, e.g., and remain attached to casing 235, if RFID is removed from filter cartridge 230. Antenna 252 may be positioned opposite integrated circuit 254 on substrate 250. Absorbent material 260 may be positioned on and/or contact antenna 252. Thus, liquid water in absorbent material 260 may deactivate antenna 252, as discussed in greater detail above. Absorbent material 260 may also be positioned on or contact casing 235. Thus, e.g., adhesive 256 may contact a portion of antenna 252, and absorbent material 260 may cover the remainder of antenna 252. Impermeable material 270 may be positioned over or on integrated circuit 254, e.g., opposite absorbent material 260.

FIG. 10 provides a section view of a third example arrangement 500 of system 240. In FIG. 10, antenna 252 is adhered to a mesh or fiber fabric 280, and adhesive 256 extends between antenna 252 and fiber fabric 280. In addition, adhesive 256 extends between fiber fabric 280 and casing 235 such that fiber fabric 280 is adhered to casing 235. Thus, e.g., antenna 252 may detach from substrate 250, e.g., and remain attached to fiber fabric 280, if RFID is removed from filter cartridge 230. Integrated circuit 254 may be positioned opposite antenna 252 on substrate 250. Absorbent material 260 may be positioned on and/or contact fiber fabric 280. Fiber fabric 280 may be liquid permeable such that liquid water may pass through fiber fabric 280 from absorbent material 260 to antenna 252. Thus, liquid water in absorbent material 260 may deactivate antenna 252, as discussed in greater detail above. Impermeable material 270 may be positioned over or on absorbent material 260, e.g., opposite fiber fabric 280.

FIG. 11 provides a section view of a fourth example arrangement 600 of system 240. In FIG. 11, absorbent material 260 is a fiber reinforced absorbent material. Thus, e.g., absorbent material 260 may include an encased mesh or reinforcing fibers that limit ripping of absorbent material 260. Antenna 252 is adhered to absorbent material 260, and adhesive 256 extends between antenna 252 and absorbent material 260. In addition, adhesive 256 extends between absorbent material 260 and casing 235 such that absorbent material 260 is adhered to casing 235. Thus, e.g., antenna 252 may detach from substrate 250, e.g., and remain attached to absorbent material 260, if RFID is removed from filter cartridge 230. Integrated circuit 254 may be positioned opposite antenna 252 on substrate 250. Absorbent material 260 may be positioned on and contact at least a portion of antenna 252, and liquid water in absorbent material 260 may deactivate antenna 252, as discussed in greater detail above. Impermeable material 270 may be positioned over or on absorbent material 260.

FIG. 12 provides a section view of a fifth example arrangement 700 of system 240. In FIG. 12, integrated circuit 254 is adhered to fiber fabric 280, and adhesive 256 extends between integrated circuit 254 and fiber fabric 280. In addition, adhesive 256 extends between fiber fabric 280 and casing 235 such that fiber fabric 280 is adhered to casing 235. Thus, e.g., integrated circuit 254 may detach from substrate 250, e.g., and remain attached to fiber fabric 280, if RFID is removed from filter cartridge 230. Antenna 252 may be positioned opposite integrated circuit 254 on substrate 250. Absorbent material 260 may be positioned on and/or contact antenna 252. Fiber fabric 280 may be liquid permeable such that liquid water may pass through fiber fabric 280 to absorbent material 260 and antenna 252. Thus, liquid water in absorbent material 260 may deactivate antenna 252, as discussed in greater detail above. Impermeable material 270 may be positioned over or on fiber fabric 280.

FIG. 13 provides a section view of a sixth example arrangement 800 of system 240. In FIG. 13, integrated circuit 254 is adhered to fiber fabric 280, and adhesive 256 extends between integrated circuit 254 and fiber fabric 280. In addition, adhesive 256 extends between fiber fabric 280 and casing 235 such that fiber fabric 280 is adhered to casing 235. Thus, e.g., integrated circuit 254 may detach from substrate 250, e.g., and remain attached to fiber fabric 280, if RFID is removed from filter cartridge 230. Antenna 252 may be positioned opposite integrated circuit 254 on substrate 250. Antenna 252 is also adhered to casing 235, and adhesive 256 extends between antenna 252 and casing 235. Thus, e.g., antenna 252 may detach from substrate 250, e.g., and remain attached to casing 235, if RFID is removed from filter cartridge 230. Absorbent material 260 may be positioned on and/or contact antenna 252. Fiber fabric 280 may be liquid permeable such that liquid water may pass through fiber fabric 280 to absorbent material 260 and antenna 252. Thus, liquid water in absorbent material 260 may deactivate antenna 252, as discussed in greater detail above. Impermeable material 270 may be positioned over or on fiber fabric 280.

FIG. 14 provides a section view of a seventh example arrangement 900 of system 240. In FIG. 14, antenna 252 is adhered to fiber fabric 280, and adhesive 256 extends between antenna 252 and fiber fabric 280. In addition, adhesive 256 extends between fiber fabric 280 and casing 235 such that fiber fabric 280 is adhered to casing 235. Thus, e.g., antenna 252 may detach from substrate 250, e.g., and remain attached to fiber fabric 280, if RFID is removed from filter cartridge 230. Integrated circuit 254 may be positioned opposite antenna 252 on substrate 250. Integrated circuit 254 is also adhered to casing 235, and adhesive 256 extends between integrated circuit 254 and casing 235. Thus, e.g., integrated circuit 254 may detach from substrate 250, e.g., and remain attached to casing 235, if RFID is removed from filter cartridge 230. Absorbent material 260 may be positioned on and/or contact fiber fabric 280. Fiber fabric 280 may be liquid permeable such that liquid water may pass through fiber fabric 280 from absorbent material 260 to antenna 252. Thus, liquid water in absorbent material 260 may deactivate antenna 252, as discussed in greater detail above. Impermeable material 270 may be positioned over or on absorbent material 260, e.g., opposite fiber fabric 280.

FIG. 15 provides a section view of an eight example arrangement 1000 of system 240. In FIG. 15, absorbent material 260 is a fiber reinforced absorbent material. Thus, e.g., absorbent material 260 may include an encased mesh or reinforcing fibers that limit ripping of absorbent material 260. Antenna 252 is adhered to absorbent material 260, and adhesive 256 extends between antenna 252 and absorbent material 260. In addition, adhesive 256 extends between absorbent material 260 and casing 235 such that absorbent material 260 is adhered to casing 235. Thus, e.g., antenna 252 may detach from substrate 250, e.g., and remain attached to absorbent material 260, if RFID is removed from filter cartridge 230. Integrated circuit 254 may be positioned opposite antenna 252 on substrate 250. Integrated circuit 254 is also adhered to casing 235, and adhesive 256 extends between integrated circuit 254 and casing 235. Thus, e.g., integrated circuit 254 may detach from substrate 250, e.g., and remain attached to casing 235, if RFID is removed from filter cartridge 230. Absorbent material 260 may be positioned on and contact at least a portion of antenna 252, and liquid water in absorbent material 260 may deactivate antenna 252, as discussed in greater detail above. Impermeable material 270 may be positioned over or on absorbent material 260, e.g., opposite fiber fabric 280.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A filter cartridge, comprising:
a casing;
a filter medium positioned within the casing;
a radio frequency identification tag positioned at an outer surface of the casing, the radio frequency identification tag comprising an antenna and an integrated circuit;
a water absorbent material positioned proximate the radio frequency identification tag such that signal communication of the radio frequency identification tag is disrupted when liquid water is disposed within the water absorbent material; and
a water impermeable material positioned over the water absorbent material and the radio frequency identification tag on the outer surface of the casing,
wherein the antenna, the integrated circuit or both the antenna and the integrated circuit are adhered to one or more of the casing, the water absorbent material and a fiber fabric positioned over the radio frequency identification tag on the outer surface of the casing.

2. The filter cartridge of claim 1, wherein the antenna is adhered to the casing such that adhesive extends between the antenna and the casing.

3. The filter cartridge of claim 1, wherein the integrated circuit is adhered to the casing such that adhesive extends between the integrated circuit and the casing.

4. The filter cartridge of claim 1, wherein the antenna is adhered to the water absorbent material such that adhesive extends between the antenna and the water absorbent material, the water absorbent material being a fiber reinforced water absorbent material, the fiber reinforced water absorbent material adhered to the casing.

5. The filter cartridge of claim 4, wherein the integrated circuit is adhered to the casing such that adhesive extends between the integrated circuit and the casing.

6. The filter cartridge of claim 1, wherein the antenna is adhered to the fiber fabric such that adhesive extends between the antenna and the fiber fabric, the fiber fabric adhered to the casing.

7. The filter cartridge of claim 6, wherein the integrated circuit is adhered to the casing such that adhesive extends between the integrated circuit and the casing.

8. The filter cartridge of claim 1, wherein the integrated circuit is adhered to the fiber fabric such that adhesive extends between the integrated circuit and the fiber fabric, the fiber fabric adhered to the casing.

9. The filter cartridge of claim 8, wherein the antenna is adhered to the casing such that adhesive extends between the antenna and the casing.

10. The filter cartridge of claim 1, wherein the water impermeable material is a plastic film and the water absorbent material is an electrolyte doped paper.

11. A filter cartridge, comprising:
a casing;
a filter medium positioned within the casing;
a radio frequency identification tag positioned at an outer surface of the casing, the radio frequency identification tag comprising an antenna and an integrated circuit;
a water absorbent material positioned proximate the radio frequency identification tag such that signal communication of the radio frequency identification tag is disrupted when liquid water is disposed within the water absorbent material; and
a water impermeable material positioned over the water absorbent material and the radio frequency identification tag on the outer surface of the casing,
wherein the antenna, the integrated circuit or both the antenna and the integrated circuit are fixedly connected to one or more of the easing and the water absorbent material.

12. The filter cartridge of claim 11, wherein the antenna, the integrated circuit or both the antenna and the integrated circuit are adhered to the easing.

13. The filter cartridge of claim 11, wherein the antenna, the integrated circuit or both the antenna and the integrated circuit are adhered to the water absorbent material, the water absorbent material being a fiber reinforced water absorbent material, the fiber reinforced water absorbent material adhered to the easing.

14. The filter cartridge of claim 11, wherein the water impermeable material is a plastic film and the water absorbent material is an electrolyte doped paper.

15. A filter cartridge, comprising:
a casing;
a filter medium positioned within the casing;
a radio frequency identification tag positioned at an outer surface of the casing, the radio frequency identification tag comprising an antenna and an integrated circuit;
a fiber reinforced water absorbent material positioned proximate the radio frequency identification tag such that signal communication of the radio frequency identification tag is disrupted when liquid water is disposed within the fiber reinforced water absorbent material; and
a water impermeable material positioned over the fiber reinforced water absorbent material and the radio frequency identification tag on the outer surface of the casing,
wherein the antenna, the integrated circuit or both the antenna and the integrated circuit are fixedly connected to the fiber reinforced water absorbent material.

16. The filter cartridge of claim 15, wherein the antenna, the integrated circuit or both the antenna and the integrated circuit are adhered or over-molded to the fiber reinforced water absorbent material.

17. The filter cartridge of claim 15, wherein the water impermeable material is a plastic film and the water absorbent material is an electrolyte doped fiber reinforced paper.

18. A filter cartridge, comprising:
a casing;
a filter medium positioned within the casing;
a radio frequency identification tag positioned at an outer surface of the casing, the radio frequency identification tag comprising an antenna and an integrated circuit;
a water absorbent material positioned proximate the radio frequency identification tag such that signal communication of the radio frequency identification tag is disrupted when liquid water is disposed within the water absorbent material;
a fiber fabric positioned over the radio frequency identification tag on the outer surface of the casing; and
a water impermeable material positioned over the water absorbent material and the radio frequency identification tag on the outer surface of the casing,
wherein the antenna, the integrated circuit or both the antenna and the integrated circuit are fixedly connected to the fiber fabric.

19. The filter cartridge of claim 18, wherein the antenna, the integrated circuit or both the antenna and the integrated circuit are adhered to the fiber fabric.

20. The filter cartridge of claim 18, wherein the water impermeable material is a plastic film and the water absorbent material is an electrolyte doped paper.

* * * * *

UNITED STATES PATENT AND TRADEMARK OFFICE
CERTIFICATE OF CORRECTION

PATENT NO.         : 10,040,009 B1
APPLICATION NO.    : 15/633932
DATED              : August 7, 2018
INVENTOR(S)        : Andrew Reinhard Krause et al.

Page 1 of 1

It is certified that error appears in the above-identified patent and that said Letters Patent is hereby corrected as shown below:

In the Claims

Claim 11: In Column 14, Line 9 - "easing" should read "casing";

Claim 12: In Column 14, Line 13 - "easing" should read "casing";

Claim 13: In Column 14, Line 19 - "easing" should read "casing".

Signed and Sealed this
Eleventh Day of December, 2018

Andrei Iancu
*Director of the United States Patent and Trademark Office*